United States Patent
Bunker

(10) Patent No.: US 10,189,780 B2
(45) Date of Patent: Jan. 29, 2019

(54) BICYCLIC ALKYL COMPOUNDS AND SYNTHESIS

(71) Applicant: Kalyra Pharmaceuticals, Inc., San Diego, CA (US)

(72) Inventor: Kevin Duane Bunker, Escondido, CA (US)

(73) Assignee: Zeno Royalties & Milestones, LLC, San Diego, CA (US)

( * ) Notice: Subject to any disclaimer, the term of this patent is extended or adjusted under 35 U.S.C. 154(b) by 0 days.

(21) Appl. No.: 15/103,038

(22) PCT Filed: Dec. 10, 2014

(86) PCT No.: PCT/US2014/069517
§ 371 (c)(1),
(2) Date: Jun. 9, 2016

(87) PCT Pub. No.: WO2015/089170
PCT Pub. Date: Jun. 18, 2015

(65) Prior Publication Data
US 2016/0311766 A1    Oct. 27, 2016

Related U.S. Application Data

(60) Provisional application No. 61/949,619, filed on Mar. 7, 2014, provisional application No. 61/915,415, filed on Dec. 12, 2013.

(51) Int. Cl.

| | |
|---|---|
| C07C 331/06 | (2006.01) |
| C07C 255/47 | (2006.01) |
| C07C 255/62 | (2006.01) |
| C07C 265/10 | (2006.01) |
| C07C 207/02 | (2006.01) |
| C07C 247/14 | (2006.01) |
| C07C 251/42 | (2006.01) |
| C07C 17/10 | (2006.01) |
| B01J 27/128 | (2006.01) |
| B01J 31/04 | (2006.01) |
| B01J 31/22 | (2006.01) |
| B01J 31/28 | (2006.01) |
| C07C 17/013 | (2006.01) |
| C07C 23/24 | (2006.01) |
| C07C 29/50 | (2006.01) |
| C07C 35/24 | (2006.01) |
| C07C 201/00 | (2006.01) |
| C07C 209/42 | (2006.01) |
| C07C 211/38 | (2006.01) |
| C07C 249/12 | (2006.01) |
| C07C 251/48 | (2006.01) |
| C07C 253/30 | (2006.01) |
| C07C 255/64 | (2006.01) |
| C07C 263/16 | (2006.01) |

(52) U.S. Cl.
CPC ........... *C07C 331/06* (2013.01); *B01J 27/128* (2013.01); *B01J 31/04* (2013.01); *B01J 31/2217* (2013.01); *B01J 31/28* (2013.01); *C07C 17/013* (2013.01); *C07C 17/10* (2013.01); *C07C 23/24* (2013.01); *C07C 29/50* (2013.01); *C07C 35/24* (2013.01); *C07C 201/00* (2013.01); *C07C 207/02* (2013.01); *C07C 209/42* (2013.01); *C07C 211/38* (2013.01); *C07C 247/14* (2013.01); *C07C 249/12* (2013.01); *C07C 251/42* (2013.01); *C07C 251/48* (2013.01); *C07C 253/30* (2013.01); *C07C 255/47* (2013.01); *C07C 255/62* (2013.01); *C07C 255/64* (2013.01); *C07C 263/16* (2013.01); *C07C 265/10* (2013.01); *B01J 2231/482* (2013.01); *B01J 2531/007* (2013.01); *B01J 2531/845* (2013.01); *C07C 2602/38* (2017.05)

(58) Field of Classification Search
CPC .................................................. C07C 331/06
See application file for complete search history.

(56) References Cited

U.S. PATENT DOCUMENTS

| | | |
|---|---|---|
| 5,262,417 A | 11/1993 | Gammill et al. |
| 5,404,550 A | 4/1995 | Horst |
| 5,405,550 A | 4/1995 | Michl et al. |
| 6,136,861 A | 10/2000 | Chenard |
| 9,447,025 B2 | 9/2016 | Bunker |
| 9,447,026 B2 | 9/2016 | Bunker |
| 9,693,975 B2 | 7/2017 | Bunker |
| 9,724,316 B2 | 8/2017 | Bunker |
| 2003/0166975 A1 | 9/2003 | Teles et al. |
| 2004/0092531 A1 | 5/2004 | Chizh et al. |
| 2006/0052370 A1 | 3/2006 | Meyerson et al. |

(Continued)

FOREIGN PATENT DOCUMENTS

| | | |
|---|---|---|
| CN | 103588668 A | 2/2014 |
| CN | 103588672 A | 2/2014 |

(Continued)

OTHER PUBLICATIONS

Bennett et al (2008):STN International, HCAPLUS database (Columbus, Ohio), Accession No. 2008: 978251.*

(Continued)

*Primary Examiner* — Golam M Shameem
(74) *Attorney, Agent, or Firm* — Knobbe, Martens, Olson & Bear, LLP

(57) ABSTRACT

Disclosed herein are compounds of the general Formula (I), and methods of synthesizing a substituted bicyclo[1.1.1] pentane using a Group VII or Group IX transition metal compound.

11 Claims, No Drawings

(56) References Cited

U.S. PATENT DOCUMENTS

| | | |
|---|---|---|
| 2007/0254862 A1 | 11/2007 | Antel et al. |
| 2009/0088418 A1 | 4/2009 | Pfister et al. |
| 2010/0056553 A1 | 3/2010 | Plettenburg et al. |
| 2012/0108583 A1 | 5/2012 | Gharat et al. |
| 2012/0122846 A1 | 5/2012 | Calerwood et al. |
| 2012/0245137 A1 | 9/2012 | Pajouhesa et al. |
| 2012/0270893 A1 | 10/2012 | Dow et al. |
| 2013/0029987 A1 | 1/2013 | Bennett et al. |
| 2013/0237559 A1 | 9/2013 | Ortiz et al. |
| 2014/0275245 A1 | 9/2014 | Bunker |
| 2015/0018328 A1 | 1/2015 | Konteatis et al. |
| 2015/0246890 A1 | 9/2015 | Bahmanyar et al. |
| 2015/0297562 A1 | 10/2015 | Iinuma et al. |
| 2016/0016892 A1 | 1/2016 | Bunker |
| 2016/0075654 A1 | 3/2016 | Bunker et al. |
| 2016/0355462 A1 | 12/2016 | Bunker |
| 2016/0374968 A1 | 12/2016 | Bunker |
| 2017/0081295 A1 | 3/2017 | Bunker |
| 2018/0042871 A1 | 2/2018 | Bunker |

FOREIGN PATENT DOCUMENTS

| | | |
|---|---|---|
| EP | 0372466 A2 | 6/1990 |
| EP | 1323725 | 7/2003 |
| IL | 54795 | 10/1980 |
| JP | 2008-120797 | 5/2008 |
| TW | 201443001 A | 11/2014 |
| WO | WO 90/06307 | 6/1990 |
| WO | WO 2000/056318 A1 | 9/2000 |
| WO | WO 2001/091736 A2 | 12/2001 |
| WO | WO 2005/063754 A1 | 7/2005 |
| WO | WO 2008/096218 A1 | 8/2008 |
| WO | WO 2009/153720 | 12/2009 |
| WO | WO 2012/137089 | 10/2012 |
| WO | WO 2012/145569 | 10/2012 |
| WO | WO 2013/024895 | 2/2013 |
| WO | WO 2013/126856 | 8/2013 |
| WO | WO 2013/131018 | 9/2013 |
| WO | WO 2014/149819 | 9/2014 |
| WO | WO 2014/169226 A2 | 10/2014 |
| WO | WO 2014/206922 A1 | 12/2014 |
| WO | WO 2015/022263 A1 | 2/2015 |
| WO | WO 2015/061247 A2 | 4/2015 |
| WO | WO 2015/089170 | 6/2015 |
| WO | WO 2015/134710 | 9/2015 |
| WO | WO 2015/157127 A1 | 10/2015 |
| WO | WO 2015/159175 A1 | 10/2015 |
| WO | WO 2015/162459 A1 | 10/2015 |
| WO | WO 2016/016370 A1 | 2/2016 |
| WO | WO 2016/044331 | 3/2016 |

OTHER PUBLICATIONS

Bunker et al., "Scalable Synthesis of 1-Bicyclo[1.1.1]pentylamine via a Hydrohydrazination Reaction" Org. Lett. (2011) 13:4746-4748.
Carey, Francis, Organic Chemistry, 2nd ed., McGraw Hill, Inc., New York (1992), pp. 328-331.
Gasper et al., "Mild Cobalt-Catalyzed Hydrocyanation of Olefins with Tosyl Cyanide" Angew. Chem., Int. Ed. (2007) 46:4519-4522.
Gasper et al., "Catalyic Hydrochlorination of Unactivated Olefins with para-Toulenesulfonyl Chloride" Angew. Chem., Int. Ed. (2008) 47:5758-5760.
Gasper et al., "Cobalt Catalyzed Functionalization of Unactivated Alkenes: Regioselective Reductive C—C Bond Forming Reactions" J. Am. Chem. Soc. (2009) 131:13214-13215.
Goh, et al., "A New Route to Bicyclo[1.1.1]pentan-1-amine from 1-Azido-3-iodobicyclo[1.1.1]pentane" Organic Letters (2014) 16(7):1884-1887.
Harvey et al., "The Cleavage of sym-Diphenyldisiloxane by Organometallic Compounds" J. Am. Chem. Soc. (1957) 79:1437-1439.
Keinan et al., "Silicon hydrides and molybdenum(0) catalyst: a novel approach for conjugate reduction of .alpha.,.beta.-unsaturated carbonyl compounds" J. Org. Chem. (1987) 52:2576-2580.
Larock *Comprehensive Organic Transformations: A Guide to Functional Group Preparations*, 2$^{nd}$ Ed., Wiley, John & Sons, Inc., Nov. 1999 (Table of Contents only).
Levin et al., "Bicyclo[1.1.1]pentanes, [n]Staffanes, [1.1.1]Propellanes, and Tricyclo[2.1.0.0$^{2,5}$]pentanes" (2000) Chem. Rev. 100:169-234.
March, *Advanced Organic Chemistry: Reactions, Mechanisms, and Structure*, 6$^{th}$ Ed., Wiley, John & Sons, Inc., Jan. 2007 (Table of Contents only).
McMurry, Organic Chemistry, 5th ed., Brooks/Cole, Pacific Grove, CA (2000), Chapter 11.5, pp. 398 and 408.
Mondanaro et al., "[1.1.1]Propellane" Org. Synth. (1998) 75:98-105.
Schaus et al., "Highly Selective Hydrolytic Kinetic Resolution of Terminal Epoxides Catalyzed by Chiral (salen)CoIII Complexes. Practical Synthesis of Enantioenriched Terminal Epoxides and 1,2-Diols" J. Am. Chem. Soc. (2002) 124:1307-1315.
Semmler et al. "Tetracyclo[5.1.0.01,6.02,7]octane, a [1.1.1]propellane derivative, and a new route to the parent hydrocarbon" J. Am. Chem. Soc. (1985) 107: 6410-6411.
Shtarev et al., "Partially Bridge-Fluorinated Dimethyl Bicyclo[1.1.1]pentane-1,3-dicarboxylates: Preparation and NMR Spectra" J. Am. Chem. Soc. (2001) 123: 3484-3492.
Streitwieser et al., Introduction to Organic Chemistry, 2nd ed., Macmillan Publishing Co. Inc., New York, NY, 1981, pp. 169-71.
Waser et al., "Hyrdazines and Azides via the Metal-Catalyzed Hydrohydrazination and Hydroazidation of Olefins" J. Am. Chem. Soc. (2006) 128:11693-11712.
Wiberg et al. "The reaction of 3-bromocyclobutane-1-methyl bromide with sodium : bicyclo[1. 1. 1]pentane" Tetrahedron Lett. (1964) 5(10):531-534.
Wiberg et al. [1.1.1]Propellane J. Am. Chem. Soc. (1982) 104:5239-5240.
International Search Report and Written Opinion dated Mar. 24, 2015 for PCT Application No. PCT/US2014/069517, filed Dec. 10, 2014.
International Preliminary Report on Patentability dated Nov. 24, 2015 for PCT Application No. PCT/US2014/069517, filed Dec. 10, 2014.
Adcock, W., et al., "Transmission of polar substituent effects across the bicyclo[1.1.1]pentane ring system as monitored by $^{19}$F NMR shifts" *Magn. Reson. Chem.* (2000) 38:115-122.
Adcock et al., "Polar Substituent Effects in the Bicyclo[1.1.1]pentane Ring System: Acidities of 3-Substituted Bicyclo[1.1.1]pentane-1-carboxylic Acids" J.Org. Chem. (2005) 70(3):1029-1034.
Adcock, W., "A DFT-GIAO and DF-NBO study of polar substituent effects on NMR $^{17}$O chemical shifts in some rigid polycyclic alkanes" *J. Phys. Org. Chem.* (2011) 24:492-498.
Applequist, D.E., et al., "Polar Substituent Effects in 1,3-Disubstituted Bicyclo[1.1.1]pentanes" *J. Org. Chem.* (1982) 47:4985-4995.
Bunz et al., Chemische Berichte (1998) 121(10):1785-1790 (RN 115092-76-7 and RN 115092-79-0).
Contreras, R.H. et al., "Experimental and DFT studies on the transmission mechanisms of analogous NMR $J_{CH}$ and $J_{CC}$ couplings in 1-X- and 1-X-3-methylbicyclo[1.1.1]-pentanes" *Magn. Reson. Chem.* (2007) 45:572-577.
Hassner, A. "e-EROS Encyclopedia of Reagents for Organic Chemistry" (2005) 1-6 (John Wiley & Sons, Ltd., Chichester) (RN 351882-60-5 and RN351882-61-6).
Janecki, T., et al., "[n]Staffanes with Terminal Nitrile and Isonitrile Functionalities and their Metal Complexes" *Collect. Czech. Chem. Commun.* (1993) 83:89-104.
Pätzel, M., et al., "3-Aminobicyclo[1.1.1]pentane-1-carboxylic Acid Derivatives: Synthesis and Incorporation into Peptides" *Eur. J. Org. Chem.* (2004):493-498.
Toops et al., "Efficient Synthesis of 1-(Trialkylstannyl)- and 1-(Triarylstannyl)bicyclo[1.1.1]pentanes" *J. Org. Chem.* (1993) 58:6505-6508.

(56) References Cited

OTHER PUBLICATIONS

Wang et al., "The Oral Analgesic Efficacy of Bicifadine Hydrochloride in Postoperative Pain" J. Clin. Pharm. (1982) 22(4):160-164.
Zehnder et al., "Optimization of Potent, Selective, and Orally Bioavailable Pyrrolodinopyrimidine-Containing Inhibitors o Heat Shock Protein 90. Identification of Development Candidate 2-Amino-4-{4-chloro-2-[2-(4-fluoro-1H-pyrazol-1-yl)ethoxy]-6-methylphenyl}-N-(2,2-difluoropropyl)-5,7-dihydro-6H-pyrrolo[3,4-d]pyrimidine-6-carboxamidef" J. Med. Chem. (2011) 54:3368-3385.
Fluck, E., "New Notations in the Periodic Table" Pure & Applied Chemistry (1988) 60(3):432-436.
IUPAC Periodic Table of the Elements (2011).
Wiberg et al., "Reactions of [1.1.1] Propellane" J. Am. Chem. Soc. (1990) 112(6):2194-2216.
Adcock et al., "Computation and analysis of $^{19}$F substituent chemical shifts of some bridgehead-substituted polycyclic alkyl fluorides" Magnetic Resonance in Chemistry (2003) 41:503-508.
Office Action dated Jan. 30, 2018 for Chinese Application No. 201480067673.7, filed Dec. 10, 2014.
Office Action and Search Report dated Feb. 12, 2018 for Taiwanese Application No. 103143524, filed Dec. 12, 2014.
Adcock, W. et al. (1992) Transmission of Polar substituent effects through the Bicyclo[1.1.1]pentane Ring System as monitored by $^{19}$F NMR shifts. Tetrahedron Letters, 33(48):7397-7398.
Alekseenko et al. (2012) An improved synthesis of 2-, 3-, and 4-(trifluoromethyl)cyclohexylamines. Synthesis. 44:2739-2742.
CAS Reg No. 1219538-79-0, STN Entry Date: Apr. 19, 2010.
CAS Reg No. 1219538-81-4, STN Entry Date: Apr. 19, 2010.
CAS Reg No. 1219538-83-6, STN Entry Date: Apr. 19, 2010.
CAS Reg No. 130974-28-6, STN Entry Date: Dec. 14, 1990.
Della, E.W. (1970) Fluorine-19 chemical shits in saturated systems. Australian journal of Chemistry. 23(12):2421-2426.
Radchenko, et al. (2010) Cyclobutane-derived diamines: synthesis and molecular structure. Journal of Organic Chemistry. 75:5941-5952.
Whitney et al. (1970) Antiviral agents. I. Bicyclo[2.2.2]octan- and -oct-2-enamines. Journal of Medicinal Chemistry. 13(2):254-260.
Office Action dated Mar. 9, 2017 for Chinese Application No. 201480067673.7, filed Dec. 10, 2014.
Supplementary European Search Report dated Jun. 19, 2017 for EP Application No. 14869147.0, filed Dec. 10, 2014.

* cited by examiner

BICYCLIC ALKYL COMPOUNDS AND SYNTHESIS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

FIELD

The present disclosure relates to synthetic organic chemistry, and in particular to [1.1.1]-bicyclopentane-based compounds (propellane derivatives) and their synthesis.

DESCRIPTION

There is significant need for new categories of small organic molecules useful as reagents in synthetic organic chemistry. Although it has been estimated that there are $10^{60}$ possible small carbon-containing molecules, only a tiny fraction of those can be effectively and efficiently synthesized using known reactions and readily-available starting materials (or "building blocks"). New building blocks or more efficient methods of synthesizing known but expensive building blocks could expand the chemical space available for exploration, for example, in areas such as pharmaceuticals, agricultural chemistry, polymers, advanced materials, and many other areas of endeavor.

One structural motif that is highly under-represented in synthetic organic chemistry is bicyclo[1.1.1]pentane (BCP) having the structure:

BCP

This is largely due to the difficulty, high cost, and low yields of BCP and its derivatives using known synthetic schemes. Although BCP has been the subject of some experimentation as a structural motif in pharmaceuticals, polymers, liquid crystal displays, high energy density materials, nanoparticles or molecular rods, macrocycles, organometallic complexes, and physical organic chemistry, compounds having a BCP structure have yet to be commercialized in those fields. In short, commercial use of BCPs has been hampered by availability and cost of reagents.

SUMMARY

Some embodiments disclosed herein relate to a method for preparing a substituted bicyclo[1.1.1]pentane compound that can include combining [1.1.1]propellane; a Group VII transition metal compound or a Group IX transition metal compound; a hydride source; and a reagent capable of contributing all or a part of a substituent group such that bicyclo[1.1.1]pentane is substituted with the substituent group.

Some embodiments described herein relate to using a method described herein to obtain a compound of Formula (I).

Some embodiments described herein relate to a compound of Formula (I).

DETAILED DESCRIPTION

Bicyclo[1.1.1]pentanes are remarkably stable, despite being highly ring-strained. The first example of an isolated bicyclo[1.1.1]pentane was reported by Wiberg in 1964 (Wiberg et al. *Tetrahedron Lett.* 1964, 531-4). However, development of the bicyclo[1.1.1]pentane field was slow due to the difficult and low yielding chemistry. Some twenty years passed before a more productive route into BCPs was discovered by Wiberg (Wiberg et al. *J. Am. Chem. Soc.* 1982, 104, 5239-40) and further developed by Sziemes (Semmler et al. *J. Am. Chem. Soc.* 1985, 107, 6410-11) that utilized the highly ring-strained [1.1.1]propellane as a starting material.

Bicyclo[1.1.1]pentane has unique properties, including shape (sterics) and polarity (electronics) where the high ring-strain creates an electron withdrawing effect for substituents on the bridgehead carbons. For example, 1-bicyclo[1.1.1]pentyl amine is significantly less basic compared to tert-butylamine (pKa of the conjugate acid is 8.6 for 1-bicyclo[1.1.1]pentyl amine vs. 11.0 for tBuNH$_2$). Likewise, 1-carboxybicyclo[1.1.1]pentane is more acidic than pivalic acid (pKa of 4.09 for 1-carboxybicyclo[1.1.1]pentanes vs. 5.05 for pivalic acid). These and other properties suggest that BCPs may find significant application as organic chemistry building blocks. Nevertheless, despite advances in synthesis of a few BCPs (see, e.g., Bunker et al., *Org. Lett.* 2011, 13, 4746-4748), there is a need for additional BCP building blocks and for more cost-effective syntheses for known BCP-based compounds.

Abbreviations

As used herein, the following terminology is defined as indicated:

| TERM | DEFINITION |
| --- | --- |
| THF | tetrahydrofuran |
| NMP | N-methyl-2-pyrrolidone |
| DMF | dimethylformamide |
| Mn(dpm)$_3$ | tris(2,2,6,6-tetramethyl-3,5-heptanedionato) manganese (III) |
| DMSO | dimethylsulfoxide |
| MTBE | methyl(tert-butyl)ether |

Definitions

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, sulfenyl, sulfinyl, sulfonyl, haloalkyl, haloalkoxy, an amino, a mono-substituted amino group and a di-substituted amino group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl, and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl, and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl, and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 3 to 10 atoms in the ring(s) or 3 to 8 atoms in the ring(s). When composed of two or more rings, the rings may be joined together in a fused, bridged or spiro fashion. A cycloalkynyl group may be unsubstituted or substituted.

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), (heteroaryl)alkyl or (heterocyclyl)alkyl. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4- thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenyl(alkyl), 3-phenyl(alkyl), and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). A lower alkylene group can be substituted by replacing one or more hydrogen of the lower alkylene group and/or by substituting both hydrogens on the same carbon with a cycloalkyl group (e.g.,

).

The term "carbonyl" used herein refers to C=O (i.e. carbon double bonded to oxygen).

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl, and acryl. An acyl may be substituted or unsubstituted.

The term "amino" used herein refers —NH$_2$.

A "mono-substituted amino" group refers to a "—NHR" group in which R can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A mono-substituted amino may be substituted or unsubstituted. Examples of mono-substituted amino groups include, but are not limited to, —NH(methyl), —NH(phenyl) and the like.

A "di-substituted amino" group refers to a "—NR$_A$R$_B$" group in which R$_A$ and R$_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A di-substituted amino may be substituted or unsubstituted. Examples of di-substituted amino groups include, but are not limited to, —N(methyl)$_2$, —N(phenyl)(methyl), —N(ethyl)(methyl) and the like.

The term "halogen atom" or "halogen" as used herein, means any one of the radio-stable atoms of column 7 of the Periodic Table of the Elements, such as, fluorine, chlorine, bromine and iodine.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "alkoxyalkyl" refers to an alkoxy group connected, as a substituent, via a lower alkylene group. Examples include alkyl-O—(CH$_2$)n-, wherein n is an integer in the range of 1 to 6.

As used herein, "acylalkyl" refers to an acyl connected, as a substituent, via a lower alkylene group. Examples include aryl-C(=O)—(CH$_2$)n- and heteroaryl-C(=O)—(CH$_2$)n-, where n is an integer in the range of 1 to 6. An acylalkyl may be substituted or unsubstituted.

As used herein, "aminoalkyl" refers to an optionally substituted amino group connected, as a substituent, via a lower alkylene group. Examples include H$_2$N—(CH$_2$)n-, (CH$_3$)$_2$N—(CH$_2$)n- and (CH$_3$)(phenyl)N—(CH$_2$)n-, wherein n is an integer in the range of 1 to 6.

As used herein, "haloalkoxy" refers to an —O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfonyl" group refers to an "SO$_2$R" group in which R can be hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A sulfenyl may be substituted or unsubstituted.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

It is to be understood that where compounds disclosed herein have unfilled valencies, then the valencies are to be filled with hydrogens or isotopes thereof, e.g., hydrogen-1 (protium) and hydrogen-2 (deuterium).

Where a range of values is provided, it is understood that the upper and lower limit, and each intervening value between the upper and lower limit of the range is encompassed within the embodiments.

Methods

Some embodiments disclosed herein relate to a method for preparing a substituted bicyclo[1.1.1]pentane compound that can include combining [1.1.1]propellane; a Group VII transition metal compound or a Group IX transition metal compound; a hydride source; and a reagent capable of contributing all or a part of a substituent group such that bicyclo[1.1.1]pentane is substituted with the substituent group.

A general synthetic route for preparing a substituted bicyclo[1.1.1]pentane compound is shown in Schemes 1 and 2, and described herein. The route shown and described herein is illustrative only and is not intended, nor is to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

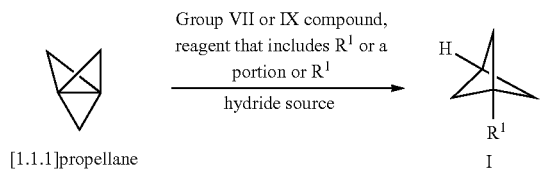

As shown in Scheme 1, the hydride source contributes the shown hydrogen and the reagent contributes $R^1$ or a portion of $R^1$ to the substituted bicyclo[1.1.1]pentane compound. As provided herein, various Group VII compounds, Group IX compounds, reagents that include $R^1$ or a portion of $R^1$ and hydride sources can be used to form a substituted bicyclo[1.1.1]pentane compound.

[1.1.1]Propellane can be prepared via various methods. Suitable methods are described by Shtarev et al., *J. Am. Chem. Soc.* 2001, 123, 3484-3492 and Lynch et al., *Org. Synth.* 1998, 75, 98-105, which are hereby incorporated by reference in their entireties. One example of a suitable method is shown in Scheme 2.

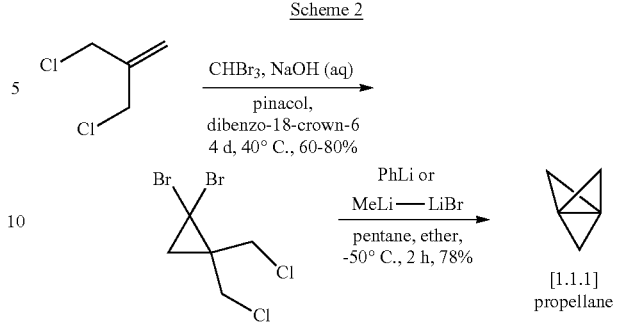

Metal-Compounds

Those skilled in the art understand that Group VII includes the following elements: cobalt, rhodium, iridium and meitnerium; and Group IX includes manganese, technetium, rhenium and bohrium. In some embodiments, the Group VII transition metal compound can be a cobalt-based transition metal compound. The oxidation state of the transition metal compound can vary. For example, in some embodiments, the oxidation state of cobalt can be Co(II), such that the Group VII transition metal compound is a Co(II)-based transition metal compound. In other embodiments, the oxidation state of cobalt can be Co(III), such that the Group VII transition metal compound is a Co(III)-based transition metal compound.

In some embodiments, the Group IX transition metal compound can be a manganese-based compound. As with cobalt, the oxidation state of the manganese of the manganese-based transition metal compound can vary. In some embodiments, the oxidation state of manganese can be Mn(II), such that the Group IX transition metal compound is a Mn(II)-based transition metal compound. In other embodiments, the oxidation state of manganese can be Mn(III), such that the Group IX transition metal compound is a Mn(III)-based transition metal compound. The Group VII and Group IX transition metal compound can be a salt, a solvate (including mono- and per-solvates) or a hydrate (including mono- and per-hydrates).

In some embodiments, the Group VII transition metal compound can include one or more ligands attached and/or coordinated to the Group VII metal, such that the Group VII transition metal compound is a Group VII transition metal complex. In some embodiments, the Group IX transition metal compound can include one or more ligands attached and/or coordinated to the Group IX metal, such that the Group IX transition metal compound is a Group IX transition metal complex. As used herein, the term "ligand" is used herein in its ordinary sense as understood by those skilled in the art, and refers to a group bound to a central atom in a chelate or a coordination compound. Examples of suitable ligands include Schiff-based ligands (such as salen-type ligands), 2-(3,5-di-tert-butyl-2-hydroxybenzylideneamino)-2,2-diphenylacetate, salicylaldehyde together with 2-aminoisobutyric acid and salicylaldehyde together with alanine. Additional examples of suitable ligands are provided below:

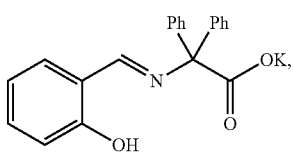

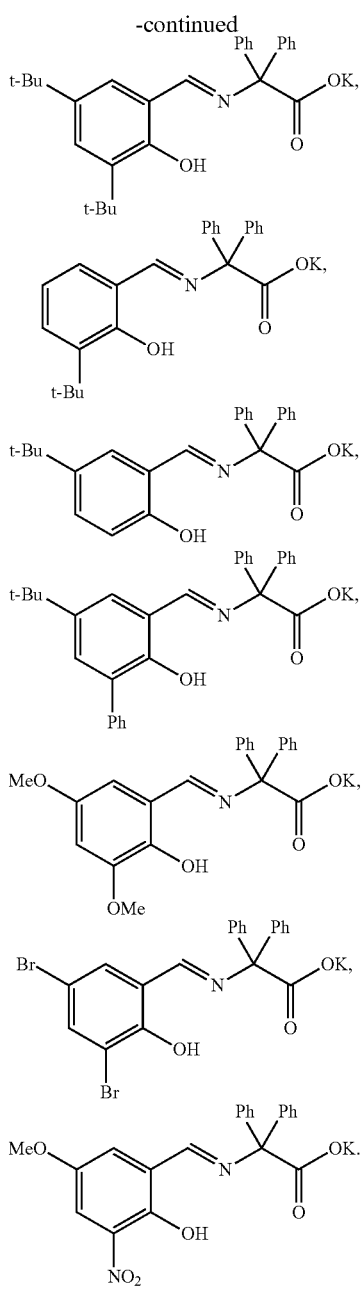

In some embodiments, more than one ligand can be present in the Group VII transition metal complex. In some embodiments, more than one ligand may be present in the Group IX transition metal complex. In some embodiments, the Group VII transition metal complex can be a cobalt-based transition metal complex. In some embodiments, the Group IX transition metal complex can be a manganese-based transition metal complex.

The amount of the Group VII transition metal compound or the Group IX transition metal compound used in a method described herein can vary. In some embodiments, the Group VII transition metal compound or the Group IX transition metal compound can be present in a stoichiometric amount. In other embodiments, the Group VII transition metal compound or the Group IX transition metal compound can be present in a catalytic amount. In still other embodiments, the Group VII transition metal compound or the Group IX transition metal compound can be present in an excess amount. Examples of suitable Group VII and Group IX transition metal compounds include the following: tris(2,2,6,6-tetramethyl-3,5-heptanedionato) manganese(III) [Mn(dpm)₃], (acetato-κO)[[rel-(1R,2R)-2,2'-[1,2-cyclohexanediylbis[(nitrilo-κN)methylidyne]]bis[4,6-bis(1,1-dimethylethyl)phenolato-κO]](2-)]cobalt(III), and [N,N'-(1,1,2,2-tetramethylethylene)bis(3,5-di-tert-butylsalicylideneiminato)]cobalt(II). Additional examples include, but are not limited to, cobalt(II) nitrate, cobalt(II) acetate, cobalt(II) chloride, cobalt(II) tetrafluoroborate, bis(2,4-pentanedionato)cobalt (Co(acac)₂, bis(2,2,6,6-tetramethyl-3,5-heptanedionato) cobalt(II), bis(1-morpholinocarbamoyl-4,4-dimethyl-1,3-pentanedio-nato)cobalt(II) (Co(modp)₂), manganese(II) acetate, and the like.

Further examples of transition metal compounds include the following:

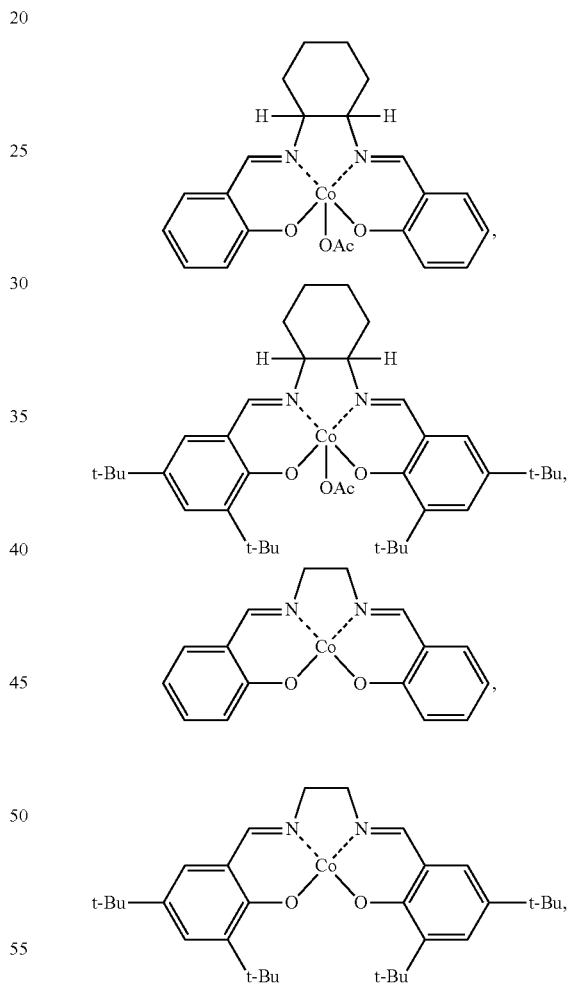

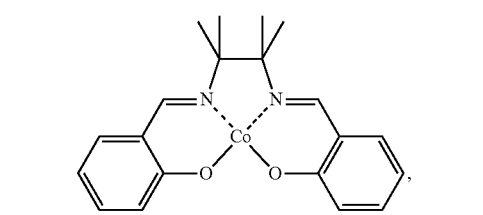

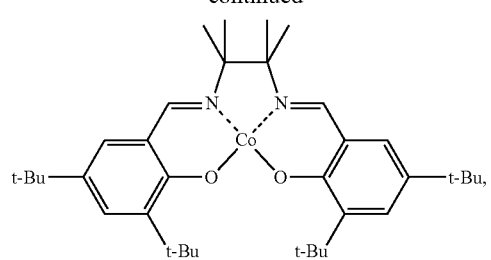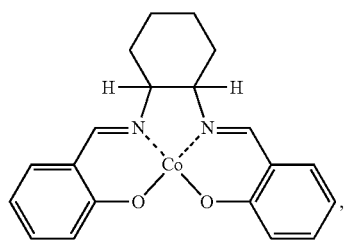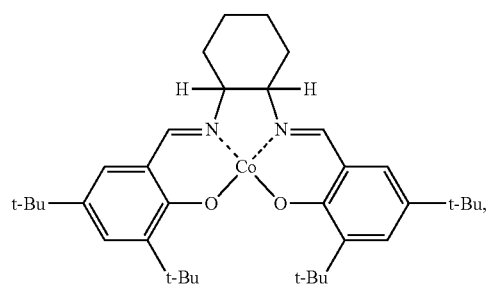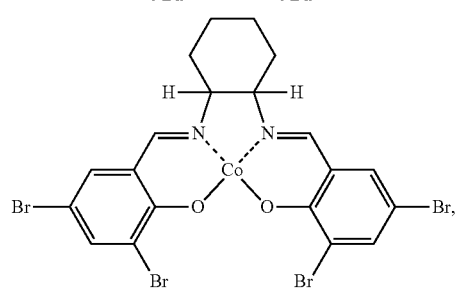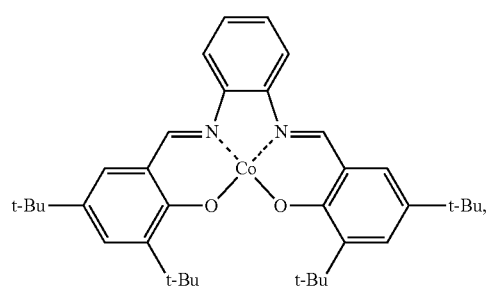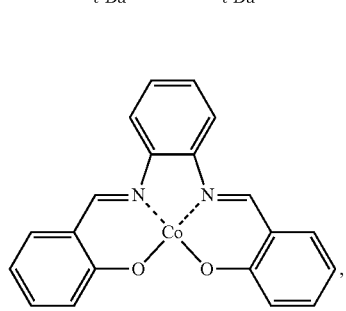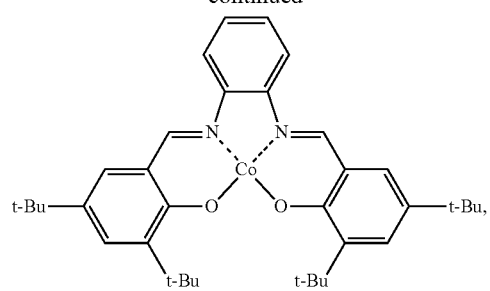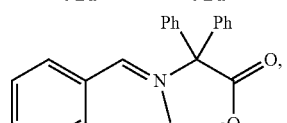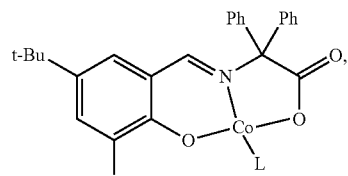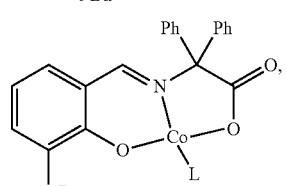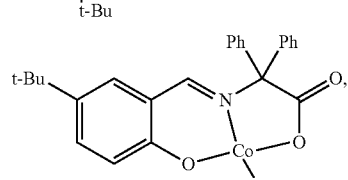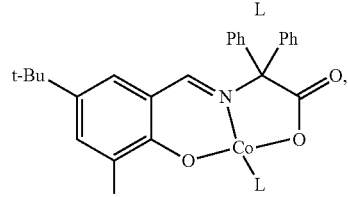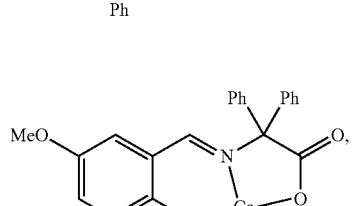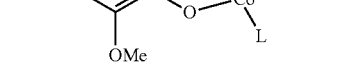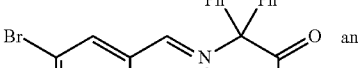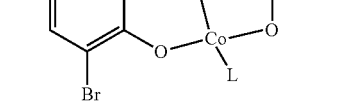

-continued

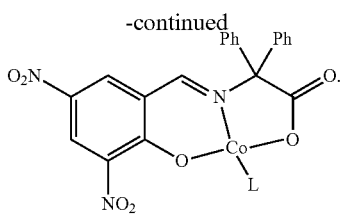

wherein L can be a coordinating solvent (for example, water, methanol, ethanol, THF, acetone, and the like). In some embodiments, the Group VII transition metal compound can be

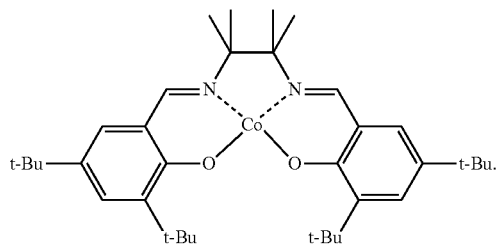

In other embodiments, the Group VII transition metal compound can be

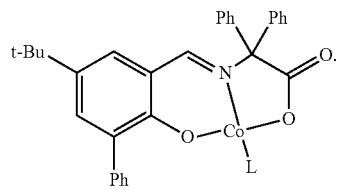

The Group VII and Group IX transition metal compounds are commercially available and/or can be prepared using methods known to those skilled in the art. Examples are provided in the following: Gaspar et al., *Angew. Chem., Int. Ed.* 2007, 46, 4519-4522; Gaspar et al., *Angew. Chem., Int. Ed.* 2008, 47, 5758-5760; Schaus et al., *J. Am. Chem. Soc.*, 2002, 124, 1307-1315; European Patent Publication EP1323725, published Jul. 2, 2003; Waser et al., *J. Am. Chem. Soc.* 2006, 128, 11693-11712; and Gaspar et al., *Am. Chem. Soc.* 2009, 131, 13214-13215, which are hereby incorporated by reference in their entireties.

Reagents

Various reagents can be used to contribute all or a part of a substituent group to the bicyclo[1.1.1]pentane compound. In some embodiments, the reagent can function as an electrophile and can trap a nucleophile. In other embodiments, the reagent can function as a radical trap of a carbon radical species to provide the substituted BCP.

In some embodiments, the reagent capable of contributing all or a part of a substituent group can have the structure $LG^1$-$R^1$, wherein $R^1$ attaches to a carbon of [1.1.1]propellane and $LG^1$ is a leaving group.

As used herein, "leaving group" refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates, mesylates, sulfonyls, and halogens (e.g., I, Br, and Cl). Non-limiting characteristics and examples of leaving groups can be found, for example in *Organic Chemistry, 2nd ed.*, Francis Carey (1992), pages 328-331; *Introduction to Organic Chemistry, 2nd ed.*, Andrew Streitwieser and Clayton Heathcock (1981), pages 169-171; and *Organic Chemistry, 5th ed.* John McMurry (2000), pages 398 and 408; all of which are incorporated herein by reference for the limited purpose of disclosing characteristics and examples of leaving groups.

In some embodiments, $LG^1$ can be an optionally substituted sulfonyl, an optionally substituted phosphonate, an alkali metal or a transition metal. Various of optionally substituted sulfonyls and optionally substituted phosphonate are suitable. In some embodiments, the optionally substituted sulfonyl can be an optionally substituted tosyl. In some embodiments, the optionally substituted phosphonate can be an optionally substituted di(alkyl)cyanophosphonate (for example, di(ethyl)cyanophosphonate).

A non-limiting list of examples of the reagents having the structure $LG^1$-$R^1$ include tosyl azide, sulfonyl azide, lithium azide, sodium azide, potassium azide, cesium azide, zinc azide, tosyl cyanide, tosyl chloride, potassium thiocyanate, potassium cyanate, sodium nitrite, (E)-(phenylsulfonyl) methanal O-benzyl oxime, (E)-N-(benzyloxy)-1-(phenylsulfonyl)methanimidoyl cyanide, diethyl phosphorocyanidate, tert-butylisocyanate, and an optionally substituted sulfonyl oxime.

In other embodiments, the reagent capable of contributing all or a part of a substituent group can have the structure $R^{1A}$-$R^{1B}$, wherein $R^{1B}$ attaches to a carbon of [1.1.1]propellane and undergoes a further transformation to form $R^1$, and $R^{1A}$ forms a byproduct. An example of $R^{1A}$-$R^{1B}$ is molecular oxygen. One oxygen atom of molecular oxygen attached to a carbon of [1.1.1]propellane and the other oxygen forms an oxide byproduct (e.g., silanoxy byproduct). A further example of a reagent capable of contributing all or a part of a substituent group having the structure $R^{1A}$-$R^{1B}$ is an optionally substituted oxaziridine.

In still other embodiments, the reagent capable of contributing all or a part of a substituent group can have the structure $R^1$. For these reagents, all the atoms of the reagent can add to a carbon of [1.1.1]propellane to form the substituted BCP. An example of this type of reagent is 2,2,6,6-tetramethyl-1-piperidinyloxy (TEMPO).

In yet still other embodiments, the reagent capable of contributing all or a part of a substituent group can have the structure of an optionally substituted $R^1$—$C_{2-10}$ alkenyl. In some embodiments, $R^1$—$C_{2-10}$ alkenyl can be unsubstituted. In other embodiments, $R^1$—$C_{2-10}$ alkenyl can be substituted. In some embodiments, the reagent capable of contributing all or a part of a substituent group can have the structure of an optionally substituted $R^1$—$C_{2-6}$ alkenyl Hydride Sources Various reagents can be used to donate a hydrogen to [1.1.1]propellane. As used herein, "hydride source" is a reagent capable of donating a H⁻ or H-radical (H•). Suitable hydride sources can transfer a hydride to [1.1.1]propellane or the metal center of the Group VII or IX transition metal compound to give a metal-hydride complex.

In some embodiments, the hydride source can be a metal-based hydride source. Examples include, but are not limited to, alkali metal-based hydrides, and alkali metal-based borohydrides (such as, sodium borohydride, sodium cyanoborohydride, lithium borohydride and sodium triacetoxyborohydride). In other embodiments, the hydride source can be a non-metal-based hydride source. Examples of non-metal-based hydride sources include, but are not limited to, silanes (for example, phenylsilane and methyldiphenylsilane), 1,1,3,3-tetramethyldisiloxane (TMDSO) and an optionally substituted borane (such as, $BH_3$, $BH_3$-complex, 9-Borabicyclo[3.3.1]nonane (9-BBN), and isopinocampheylborane).

Hydride source reagents can be obtained from commercial vendors and/or prepared utilizing methods known to those skilled in the art. The deuterated equivalents can also be obtained from commercial vendors and/or prepared using commercially available reagents, for example, as described in Keinan et al., *J. Org. Chem.*, 1987, 52, 2576-2580 and Harvey et al., *J. Am. Chem. Soc.*, 1957, 79, 1437-1439. which are hereby incorporated by reference in their entireties. In some embodiments, a method provided herein can include adding a first portion of a hydride source and a second portion of a hydride source.

The amounts of [1.1.1]propellane, the Group VII or Group IX transition metal compound, the hydride source and the reagent capable of contributing all or a part of a substituent group can vary. In some embodiments, one or more of the [1.1.1]propellane, the Group VII or Group IX transition metal compound, the hydride source and the reagent capable of contributing all or a part of a substituent group can be in excess to another one or more of the aforementioned compounds. In some embodiments, the reagent capable of contributing all or a part of a substituent group can be in excess of [1.1.1]propellane and/or the hydride source. In other embodiments, the hydride source can be in excess of [1.1.1]propellane and/or the reagent capable of contributing all or a part of a substituent group. In still other embodiments, [1.1.1]propellane can be in excess of the hydride source and/or the reagent capable of contributing all or a part of a substituent group. The amount in excess can vary. For example, the amount in excess can be about 1.2 times or more, about 1.5 times or more, about 2 times or more, about 3 times or more, or about 4 times or more. In other embodiments, one or more of [1.1.1]propellane, the Group VII or Group IX transition metal compound, the hydride source and the reagent capable of contributing all or a part of a substituent group can be in approximately equal molar amounts to another one or more of the aforementioned compounds.

The order in which each of [1.1.1]propellane, the Group VII or Group IX transition metal compound, the hydride source and the reagent capable of contributing all or a part of a substituent group are combined can also vary. For example, the Group VII or Group IX transition metal compound can be combined with the reagent capable of contributing all or a part of a substituent group, followed by the addition of [1.1.1]propellane and the hydride source. Alternatively, [1.1.1]propellane can be added before the reagent capable of contributing all or a part of a substituent group.

Additional Compounds

In some embodiments, a method described herein can include one or more additional compounds. For example, a method described herein can also include an additional compound that can act as an initiator. An initiator can generate a reactive radical species to facilitate the reaction.

In some embodiments, a method described herein can also include a compound that can act as a trapping compound. As an example, a trapping compound can combine with a byproduct of one of the compounds formed in a method described herein and can reduce the number of side reaction(s) and/or the amount of side products formed during the reaction. In other embodiments, the trapping compound can be a radical trapping compound. An example of a radical trapping compound is butylated hydroxytoluene (BHT).

In some embodiments, a method described herein can also include an additional compound that can act as an additive. As used herein, an "additive" facilitates the regeneration of a reactive compound. For example, an additive can regenerate the reactive transition metal compound. Suitable additional compounds that can be used in a methods descried herein include, for example, tert-butyl hydroperoxide, benzoyl peroxide, di-tert-butyl peroxide, 2,2'-azobis(2-methylpropionitrile) (AIBN), methylmorpholine oxide, potassium hexacyanoferrate(III), oxygen, sodium periodate, silver bromoate, silver chloroformate, ceric ammonium nitrate, hydrogen peroxide, sodium hypochlorite, Oxone®, 3-chloroperbenzoic acid, and the like.

One or more additional compounds can be included in a method provided herein at various points. Likewise, various amounts of one or more additional compounds can be included in a method provided herein. The timing and amounts of additional compounds to include in a methods provided herein is within the knowledge of those skilled in the art.

Solvents

A variety of solvents can be utilized in the methods described herein. In some embodiments, the solvent can be an alcohol-based solvent. In some embodiments, a co-solvent can be used in a method described herein. Suitable solvents and co-solvents include, but are not limited to, ethanol, methanol, isopropanol, $H_2O$, THF, $Et_2O$, NMP, DMF, DMSO, MTBE, $CH_3CN$, $CH_2Cl_2$, toluene, or dioxane, and mixtures thereof. In some embodiments, the solvent can be $H_2O$. In other embodiments, the solvent can be THF. In some embodiments, the solvent and co-solvent combination can be $H_2O$ and THF. In some embodiments, the solvent can be isopropanol. In some embodiments, the solvent can be a solvent system of methanol and $Et_2O$.

Time and Temperature

The methods provided herein can be conducted at various temperatures. Further, the temperature can be lowered and/or raised during the method. In some embodiments, the temperature can be in the range of about −5° C. to about 30° C. In some embodiments, the temperature can be room temperature (about 25° C.). In other embodiments, temperature can be about 0° C. In some embodiments, the temperature can be greater 30° C. In other embodiments, the temperature can be less than 0° C.

The time can also vary for a method described herein. For example, the time of a method provided herein can be in the range of about 30 minutes to about 3 hours. In some embodiments, the time can be in the range of about 10 hours to about 24 hours.

As provided herein, the $R^1$ that is first attached to the BCP can undergo further transformations to form other $R^1$ groups. For example, an $R^1$ group can be reduced using methods known to those skilled in the art to form other $R^1$ groups. Examples of further transformations include reduction, oxidation, addition, elimination, condensation, coupling, metathesis, rearrangements, cyclizations, aromatization, annulations, fragmentations, substitutions, transfers, homologations, and multicomponent reactions. As a specific example, an azide can be reduced using methods known to those skilled in the art to form an amino group. Further examples of suitable transformations are provided in Richard C. Larock *Comprehensive Organic Transformations: A Guide to Functional Group Preparations* ($2^{nd}$ Ed., Wiley, John & Sons, Inc., November 1999); and Jerry March, (*Advanced Organic Chemistry: Reactions, Mechanisms, and Structure* (6th Ed., Wiley, John & Sons, Inc., January 2007).

Compounds

Some embodiments disclosed herein relate to a compound of Formula (I):

(I)

wherein: $R^1$ can be $N_3$, $CF_3$, F, Cl, Br, I, CN, OH, SCN, NCO, NO, —C(=NOR$^2$)(CN), or —CH(=NOR$^2$), and $R^2$ can be ($C_1$ to $C_{10}$) alkoxy, substituted or unsubstituted ($C_1$ to $C_{30}$) alkyl, substituted or unsubstituted aryl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycle, substituted or unsubstituted heteroaryl, substituted or unsubstituted aryl(alkyl), substituted or unsubstituted alkyl(aryl), or substituted or unsubstituted heteroaryl(alkyl).

One or more methods described herein can be used to obtain a compound of Formula (I). For example, in some embodiments, $R^1$ can be $N_3$, SCN, —C(=NOR$^2$)(CN) or —CH(=NOR$^2$). In other embodiments, $R^1$ can be $CF_3$, F, Cl, Br, I, CN, OH or NCO. In some embodiments, $R^1$ can be $N_3$. In other embodiments, $R^1$ can be $CF_3$. In still other embodiments, $R^1$ can be F. In yet still other embodiments, $R^1$ can be Cl. In some embodiments, $R^1$ can be Br. In other embodiments, $R^1$ can be I. In still other embodiments, $R^1$ can be CN. In still other embodiments, $R^1$ can be OH. In yet still other embodiments, $R^1$ can be SCN. In some embodiments, $R^1$ can be NCO. In other embodiments, $R^1$ can be NO. In still other embodiments, $R^1$ can be —C(=NOR$^2$)(CN). In yet still other embodiments, $R^1$ can be —CH(=NOR$^2$).

As provided herein, $R^2$ can be a variety of groups. For example, $R^2$ can be ($C_1$ to $C_{10}$) alkoxy, substituted or unsubstituted ($C_1$ to $C_{30}$) alkyl, substituted or unsubstituted aryl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted heteroaryl, substituted or unsubstituted aryl(alkyl), substituted or unsubstituted alkyl(aryl), or substituted or unsubstituted heteroaryl(alkyl). In some embodiments, $R^2$ can be an optionally substituted benzyl. In some embodiments, OR$^2$ can be carbimidoyl cyanide, carbaldehyde oxime, (benzyloxy) carbimidoyl cyanide or carbaldehyde O-benzyl oxime.

A non-limiting list of compounds of Formula (I) include the following:

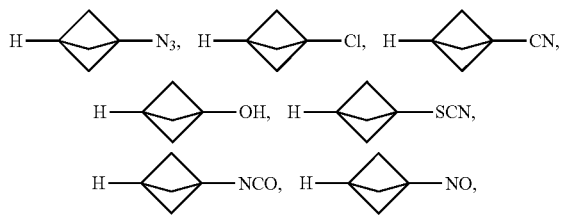

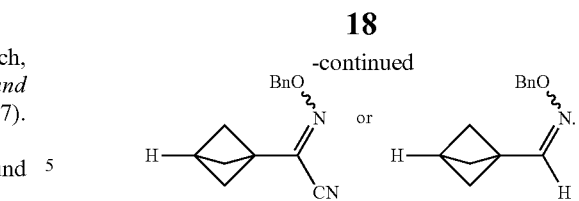

In some embodiments, $R^1$ cannot be $N_3$. In other embodiments, $R^1$ cannot be $CF_3$. In still other embodiments, $R^1$ cannot be F. In yet still other embodiments, $R^1$ cannot be Cl. In some embodiments, $R^1$ cannot be Br. In other embodiments, $R^1$ cannot be I. In still other embodiments, $R^1$ cannot be CN. In still other embodiments, $R^1$ cannot be OH. In yet still other embodiments, $R^1$ cannot be SCN. In some embodiments, $R^1$ cannot be NCO. In other embodiments, $R^1$ cannot be NO. In still other embodiments, $R^1$ cannot be —C(=NOR$^2$)(CN). In yet still other embodiments, $R^1$ cannot be —CH(=NOR$^2$).

In some embodiments, a compound of Formula (I) cannot be

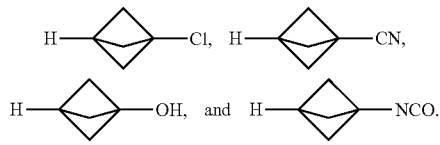

In other embodiments, a compound of Formula (I) cannot be

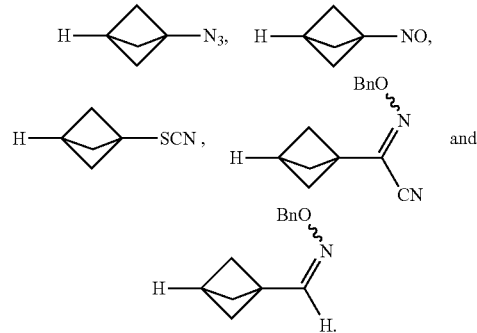

Additional details for preparing substituted bicyclo[1.1.1] pentane compounds are provided in Table 1.

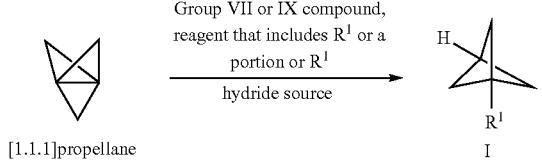

TABLE 1

| Reagent for $R^1$ | Group VII or IX compound | Hydride Source | Product |
|---|---|---|---|
| TsN$_3$ | Mn(dpm)$_3$ | PhSiH$_3$ | H—◇—N$_3$ |

TABLE 1-continued

| Reagent for R¹ | Group VII or IX compound | Hydride Source | Product |
|---|---|---|---|
| TsCl | Mn(dpm)₃ | PhSiH₃ |  |
| TsCN | Mn(dpm)₃ | PhSiH₃ |  |
| 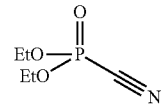 | Mn(dpm)₃ | PhSiH₃ |  |
| O₂ | Mn(dpm)₃ | PhSiH₃ |  |
| KSCN | Mn(dpm)₃ | PhSiH₃ |  |
| KOCN | Mn(dpm)₃ | PhSiH₃ |  |
| NaNO₂ | Mn(dpm)₃ | PhSiH₃ |  |
| 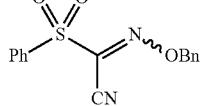 | Mn(dpm)₃ | PhSiH₃ |  |
| 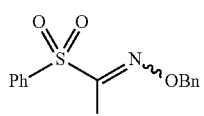 | Mn(dpm)₃ | PhSiH₃ |  |
| R¹—C₂₋₁₀ alkenyl* | Mn(dpm)₃ | PhSiH₃ | R¹—C₂₋₁₀ alkyl* |
| TsN₃ | Co(t-butyl-salen) | PhSiH₃ |  |
| TsCl | Co(t-butyl-salen) | PhSiH₃ |  |
| TsCN | Co(t-butyl-salen) | PhSiH₃ |  |
| 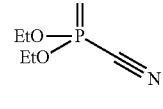 | Co(t-butyl-salen) | PhSiH₃ |  |
| O₂ | Co(t-butyl-salen) | PhSiH₃ |  |
| KSCN | Co(t-butyl-salen) | PhSiH₃ |  |
| KOCN | Co(t-butyl-salen) | PhSiH₃ | 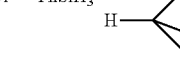 |
| NaNO₂ | Co(t-butyl-salen) | PhSiH₃ | 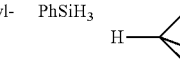 |
| 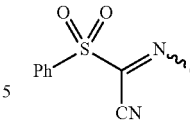 | Co(t-butyl-salen) | PhSiH₃ | 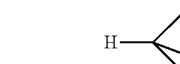 |
| 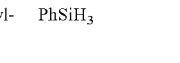 | Co(t-butyl-salen) | PhSiH₃ | 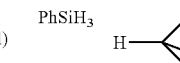 |
| R¹—C₂₋₁₀ alkenyl* | Co(t-butyl-salen) | PhSiH₃ | R¹—C₂₋₁₀ alkyl* |
| TsN₃ | Co(sal-diphenyl) | PhSiH₃ | 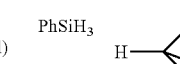 |
| TsCl | Co(sal-diphenyl) | PhSiH₃ | 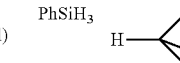 |
| TsCN | Co(sal-diphenyl) | PhSiH₃ | 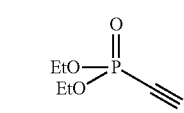 |
|  | Co(sal-diphenyl) | PhSiH₃ | 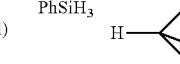 |
| O₂ | Co(sal-diphenyl) | PhSiH₃ | 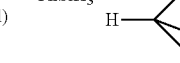 |
| KSCN | Co(sal-diphenyl) | PhSiH₃ | 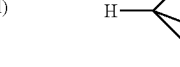 |
| KOCN | Co(sal-diphenyl) | PhSiH₃ |  |
| NaNO₂ | Co(sal-diphenyl) | PhSiH₃ | 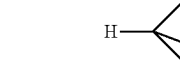 |
| 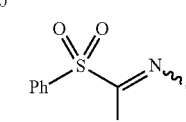 | Co(sal-diphenyl) | PhSiH₃ |  |

TABLE 1-continued

| Reagent for R¹ | Group VII or IX compound | Hydride Source | Product |
|---|---|---|---|
| R¹—C$_{2-10}$ alkenyl* | Co(sal-diphenyl) | PhSiH$_3$ | R¹—C$_{2-10}$ alkyl* |

*indicates that the alkenyl and alkyl can be optionally substituted

It should be noted that one skilled in the art would know how to modify the procedures set forth in the illustrative schemes and examples to arrive at the desired products.

EXAMPLES

Example 1: General Procedure

A solution of catalyst A or B (2-5 mol %) was dissolved in either a 3:1 or 2:1 mixture of anhydrous MeOH and anhydrous Et$_2$O containing 1 ppm BHT (10 mM final concentration) and stirred under N$_2$ for 2 mins. Propellane (1 eq.) and the appropriate trapping agent (1.2-1.5 eq.) were added followed by PhSiH$_3$ (1.0 eq.). After stirring overnight at RT (room temperature), the mixture was concentrated to afford the desired compound that was either further purified by flash chromatography on silica gel or used without further purification.

Catalyst A

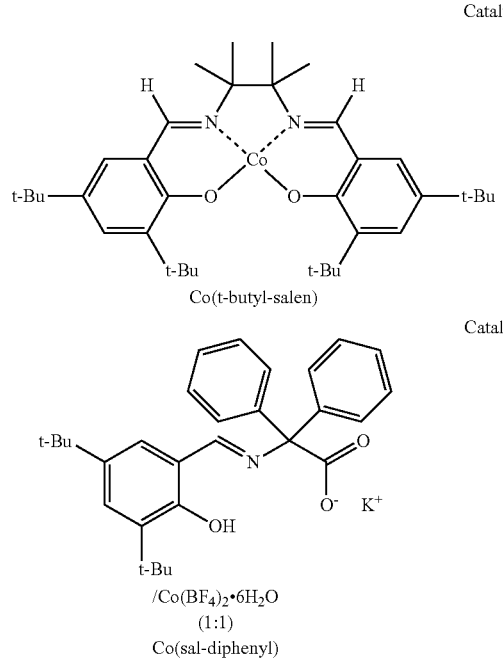

Co(t-butyl-salen)

Catalyst B

/Co(BF$_4$)$_2$·6H$_2$O
(1:1)
Co(sal-diphenyl)

Example 2: bicyclo[1.1.1]pentane-1-carbonitrile

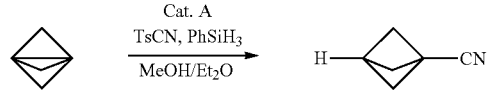

Bicyclo[1.1.1]pentane-1-carbonitrile was prepared according to the general procedure of Example 1 using tosyl cyanide, catalyst A and phenylsilane in MeOH/Et$_2$O. $^1$H NMR (400 MHz, MeOH-d4) δ 2.40 (s, 1H), 2.31 (s, 6H).

Example 3: N-(benzyloxy)bicyclo[1.1.1]pentane-1-carbimidoyl cyanide

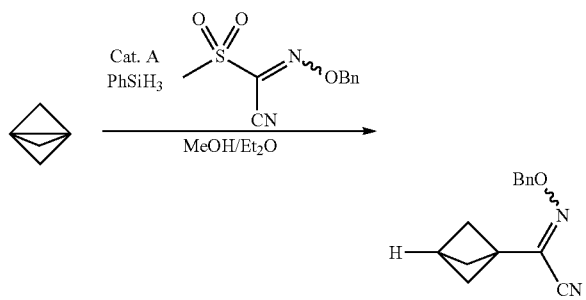

N-(benzyloxy)bicyclo[1.1.1]pentane-1-carbimidoyl cyanide was prepared according to the general procedure of Example 1 using N-(benzyloxy)-1-(methylsulfonyl)methanimidoyl cyanide, catalyst A and phenylsilane in MeOH/Et$_2$O. The product was isolated as a mixture of isomers (E and Z). Major isomer: $^1$H NMR (400 MHz, MeOH-d4) δ 7.37-7.33 (m, 5H), 5.24 (s, 2H, 2.53 (s, 1H), 2.07 (s, 6H). Minor isomer: $^1$H NMR (400 MHz, MeOH-d4) δ 7.37-7.33 (m, 5H), 5.22 (s, 1H), 2.51 (s, 1H), 2.19 (s, 6H).

Example 4: bicyclo[1.1.1]pentane-1-carbaldehyde O-benzyl oxime

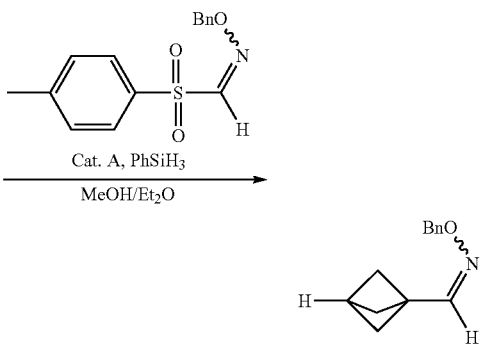

N-(benzyloxy)bicyclo[1.1.1]pentane-1-carbimidoyl cyanide was prepared according to the general procedure of Example 1 using tosylmethanal O-benzyl oxime, catalyst A and phenylsilane in MeOH/Et$_2$O. LC/MS (APCI) m/z 202.1 [C$_{13}$H$_{15}$NO+H$^+$].

Example 5: 1-azidobicyclo[1.1.1]pentane and 1-aminobicyclo[1.1.1]pentane

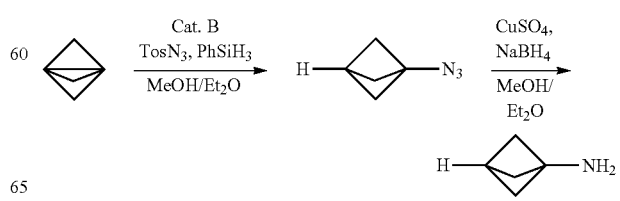

1-azidobicyclo[1.1.1]pentane was prepared according to the general procedure of Example 1 using tosyl azide, catalyst B and phenylsilane in MeOH/Et₂O.

To the crude azide from the previous step in MeOH/Et₂O was added a suspension of CuSO₄ (0.1 eq.), NaBH₄ (1 eq.) in MeOH at 0° C. NaBH₄ (4 eq.) was added portionwise over 1 h. The mixture was stirred overnight, and then acidified with 4N HCl in dioxane. The mixture was then concentration to dryness followed by trituration with Et₂O to afford 1-aminobicyclo[1.1.1]pentane. LC/MS (APCI) m/z 84.1 [C₅H₉N+H]⁺.

Those skilled in the art understand that 1-aminobicyclo[1.1.1]pentane is formed from 1-azidobicyclo[1.1.1]pentane using the conditions described herein. (See Goh, Y. L., et al., *Organic Letters* 2014, 16(7), 1884-1887). Therefore, obtaining 1-aminobicyclo[1.1.1]pentane from the conditions described herein is evidence of the formation of 1-azidobicyclo[1.1.1]pentane from BCP using tosyl azide, catalyst B and phenylsilane in MeOH/Et₂O.

Example 6: 1-chlorobicyclo[1.1.1]pentane

Under a nitrogen atmosphere, Mn(dpm)₃ (0.02 mmol) is dissolved in iso-propanol (5 mL) at room temperature and then cooled to 0° C. Phenylsilane (1 mmol) and tosyl chloride (1.5 mmol; addition reagent) dissolved in dichloromethane (5 mL) are added, followed by the addition of [1.1.1]propellane solution (1 mmol, ~0.2-0.5 M ether/pentane solution). The resulting mixture is stirred at 0° C. for 21 h. The reaction is quenched by adding water and brine. The mixture is stirred 5 min and then extracted with ethyl acetate. The combined organic layers are dried (MgSO₄), filtered and the volatiles removed under reduced pressure. The crude residue is then used in the next step, otherwise it is subjected to flash chromatography to give 1-chlorobicyclo[1.1.1]pentane.

Example 7: bicyclo[1.1.1]pentan-1-ol

The general procedure of Example 6 is repeated using oxygen as an addition reagent, and to produce bicyclo[1.1.1]pentan-1-ol. Alternatively, the general procedure of Example 1 is followed using the appropriate reagents.

Example 8: 1-thiocyanatobicyclo[1.1.1]pentane

The general procedure of Example 6 is repeated using potassium thiocyanate as an addition reagent, producing 1-thiocyanatobicyclo[1.1.1]pentane. Alternatively, the general procedure of Example 1 is followed using the appropriate reagents.

Example 9: 1-isocyanatobicyclo[1.1.1]pentane

The general procedure of Example 6 is repeated using potassium cyanate as addition reagent, to produce 1-isocyanatobicyclo[1.1.1]pentane. Alternatively, the general procedure of Example 1 is followed using the appropriate reagents.

Example 10: 1-nitrosobicyclo[1.1.1]pentane

The general procedure of Example 6 is repeated using sodium nitrite as an addition reagent, to produce 1-nitrosobicyclo[1.1.1]pentane. Alternatively, the general procedure of Example 1 is followed using the appropriate reagents.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound having the structure of Formula (I):

(I)

wherein:
R¹ is N₃, SCN, NO, —C(═NOR²)(CN), or —CH(═NOR²), and
R² is (C₁ to C₁₀) alkoxy, substituted or unsubstituted (C₁ to C₃₀) alkyl, substituted or unsubstituted aryl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycle, substituted or unsubstituted heteroaryl, substituted or unsubstituted aryl(alkyl), substituted or unsubstituted alkyl(aryl), or substituted or unsubstituted heteroaryl(alkyl).

2. The compound of claim 1, wherein R¹ is N₃, SCN, —C(═NOR²)(CN), or —CH(═NOR²).

3. The compound of claim 1, wherein OR² is carbimidoyl cyanide, carbaldehyde oxime, (benzyloxy) carbimidoyl cyanide, or carbaldehyde O-benzyl oxime.

4. The compound of claim 1, wherein $R^2$ is benzyl.

5. The compound of claim 1, having the structure

6. The compound of claim 1, having the structure

7. The compound of claim 1, having the structure

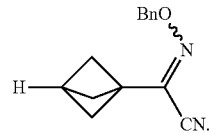 [SMILES: N#CC(=NOCc1ccccc1)C12CC(C1)C2]

8. The compound of claim 1, having the structure

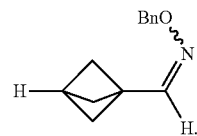

9. The compound of claim 1, having the structure

10. The compound of claim 1, wherein $R^1$ is —C(=NOR$^2$)(CN).

11. The compound of claim 1, wherein $R^1$ is —CH(=NOR$^2$).

\* \* \* \* \*

UNITED STATES PATENT AND TRADEMARK OFFICE
CERTIFICATE OF CORRECTION

PATENT NO. : 10,189,780 B2
APPLICATION NO. : 15/103038
DATED : January 29, 2019
INVENTOR(S) : Kevin Duane Bunker It is certified that error appears in the above-identified patent and that said Letters Patent is hereby corrected as shown below:

On the Title Page

Page 2 item [56], Column 2 Line 50, change "DF-NBO" to --DFT-NBO--.

In the Specification

Column 7 Line 49, Change "or" to --of--.

Column 14 Line 55, After "alkenyl" insert --.--.

Column 15 Line 16, Change "which" to --, which--.

Column 16 Line 14-15, Change "bromoate," to --bromate,--.

Column 18 Line 54, Change "or" to --of--.

Column 23 Line 3, Change "phenysilane" to --phenylsilane--.

Column 23 Line 20, Change "phenysilane" to --phenylsilane--.

Signed and Sealed this
Thirtieth Day of July, 2019

Andrei Iancu
*Director of the United States Patent and Trademark Office*